(12) United States Patent
Fausett et al.

(10) Patent No.: US 8,292,831 B2
(45) Date of Patent: Oct. 23, 2012

(54) METHOD OF MEASURING FETAL HEAD ORIENTATION, POSITION, AND VELOCITY AND PROVIDING FEEDBACK TO MOTHER AND DOCTOR

(75) Inventors: Merlin Bardett Fausett, San Antonio, TX (US); Jonathan William Hander, Allen, TX (US); Edwin William Hander, Columbia, MO (US)

(73) Assignee: OB Technologies, LLC, San Antonio, TX (US)

( * ) Notice: Subject to any disclaimer, the term of this patent is extended or adjusted under 35 U.S.C. 154(b) by 344 days.

(21) Appl. No.: 12/354,942

(22) Filed: Jan. 16, 2009

(65) Prior Publication Data

US 2010/0185122 A1    Jul. 22, 2010

(51) Int. Cl.
*A61B 5/103* (2006.01)
*A61B 5/117* (2006.01)

(52) U.S. Cl. ......................... 600/588; 600/587
(58) Field of Classification Search ............... 600/587, 600/588
See application file for complete search history.

(56) References Cited

U.S. PATENT DOCUMENTS

| | | | |
|---|---|---|---|
| 3,580,242 A | 5/1971 | La Croix | |
| 4,476,871 A | 10/1984 | Hon | |
| 4,942,882 A | 7/1990 | Bellinson | |
| 5,135,006 A | 8/1992 | Bellinson | |
| 5,222,485 A | 6/1993 | Jerath | |
| 5,405,356 A * | 4/1995 | Hahn et al. | 606/202 |
| 5,551,424 A | 9/1996 | Morrison et al. | |
| 5,566,680 A | 10/1996 | Urion et al. | |
| 5,632,274 A | 5/1997 | Quedens et al. | |
| 5,666,959 A | 9/1997 | Deans et al. | |
| 5,935,061 A * | 8/1999 | Acker et al. | 600/304 |
| 5,951,497 A | 9/1999 | Wallace et al. | |
| 6,186,945 B1 | 2/2001 | Gardosi | |
| 6,270,458 B1 * | 8/2001 | Barnea | 600/438 |
| 6,434,418 B1 | 8/2002 | Neal et al. | |
| 6,529,753 B1 | 3/2003 | Gardosi | |
| 6,669,653 B2 * | 12/2003 | Paltieli | 600/588 |
| 6,719,686 B2 | 4/2004 | Coakley et al. | |
| 6,816,744 B2 | 11/2004 | Garfield et al. | |
| 7,207,941 B2 | 4/2007 | Sharf | |
| 7,336,985 B2 | 2/2008 | Wallace et al. | |
| 2006/0015036 A1 | 1/2006 | Paltieli | |
| 2007/0225584 A1 | 9/2007 | Gravenstein et al. | |
| 2008/0167553 A1 | 7/2008 | Paltieli et al. | |
| 2008/0183092 A1 | 7/2008 | Smith et al. | |
| 2008/0221420 A1 | 9/2008 | Grubac et al. | |
| 2009/0012432 A1 * | 1/2009 | Sharf | 600/588 |

* cited by examiner

*Primary Examiner* — Jeffrey G Hoekstra
*Assistant Examiner* — Charles Becker
(74) *Attorney, Agent, or Firm* — Arent Fox LLP

(57) ABSTRACT

A method is described to provide real-time fetal position, movement velocity, and head orientation feedback to professional medical staff and delivering mothers. Using this feedback, the mother can be apprised of how effective her pushing is moving the baby through the birth canal. Medical staff can use this feedback to assess fetal head orientation and determine location of the baby in the birth canal. The feedback device consists of metrology devices mounted on a fetal scalp electrode, a data acquisition method, software to interpret the metrology signals, and feedback hardware for doctors and the mother.

32 Claims, 1 Drawing Sheet

METHOD OF MEASURING FETAL HEAD ORIENTATION, POSITION, AND VELOCITY AND PROVIDING FEEDBACK TO MOTHER AND DOCTOR

This invention relates to the hardware and methods used during childbirth. The present invention relates particularly to a method of delivering fetal head orientation, position, and rate of decent information to the mother and delivery-room staff to shorten delivery-time and reduce vaginal examinations during labor.

BACKGROUND OF THE INVENTION

Regional anesthesia, including epidurals, is commonly used during labor. Childbirth under regional anesthesia inhibits the natural physiologic feedback from the nervous system that causes effective maternal expulsive efforts. Because of the lack of natural sensory feedback, mothers—especially those who are experiencing child-birth for the first time—lack the natural sensation, inherent urge and ability to generate effective pushing. This prolongs labor that leads to increased maternal, fetal, and neonatal morbidity and mortality and an increased time burden on the delivery staff and facilities.

With additional coaching from knowledgeable delivery attendants, the mother can be provided with extra-biological feedback improving her ability to successfully move the baby through the birth canal. The most effective coaching involves the ability to provide the mother immediate feedback and guidance in response to her expulsive efforts. This typically requires frequent or even constant digital vaginal examinations to evaluate fetal position and descent. However, these vaginal examinations increase the risk of maternal and fetal infection and tissue trauma. In addition to the health risks of coaching using vaginal examination, such a coaching process requires the direct time attention of professional attendants. This adds to the time-burden of the delivery-room staff.

Knowing the fetal head position during labor increases the ability of the attending staff to intervene when necessary to facilitate effective pushing. This also typically requires multiple vaginal examinations with the associated risks previously described.

Accordingly, it is desirable to have a method that provides immediate feedback to the mother and attendant staff, without requiring digital vaginal examinations, that allows timely intervention and maximizes the effectiveness of maternal expulsive efforts.

BRIEF SUMMARY OF THE INVENTION

In accordance with one aspect of the present invention, a device is used to monitor the fetal descent and velocity of the baby with respect to a fixed position during labor. The data from this device are then processed and used to provide feedback to the mother enabling her to push more effectively. Said feedback can simultaneously provide information to the delivery room staff enabling them to intervene in a timely and effective manner.

A separate sensor, that can be integrated into the same device, detects fetal head rotation and orientation in real-time. The metrology device and resultant measurements, independently or collectively provide information facilitating maximally effective expulsive efforts without the need for frequent vaginal examination. Minimizing digital examinations and shortening the delivery process reduces maternal and fetal morbidity and mortality.

The present invention will be more fully understood in light of the following detailed description taken together with the accompanying drawings.

BRIEF DESCRIPTION OF THE SEVERAL VIEWS OF THE DRAWING

For a more complete understanding of the present invention, reference is now made to the following descriptions taken in conjunction with the accompanying drawing in which.

DETAILED DESCRIPTION OF THE INVENTION

Figure 1:
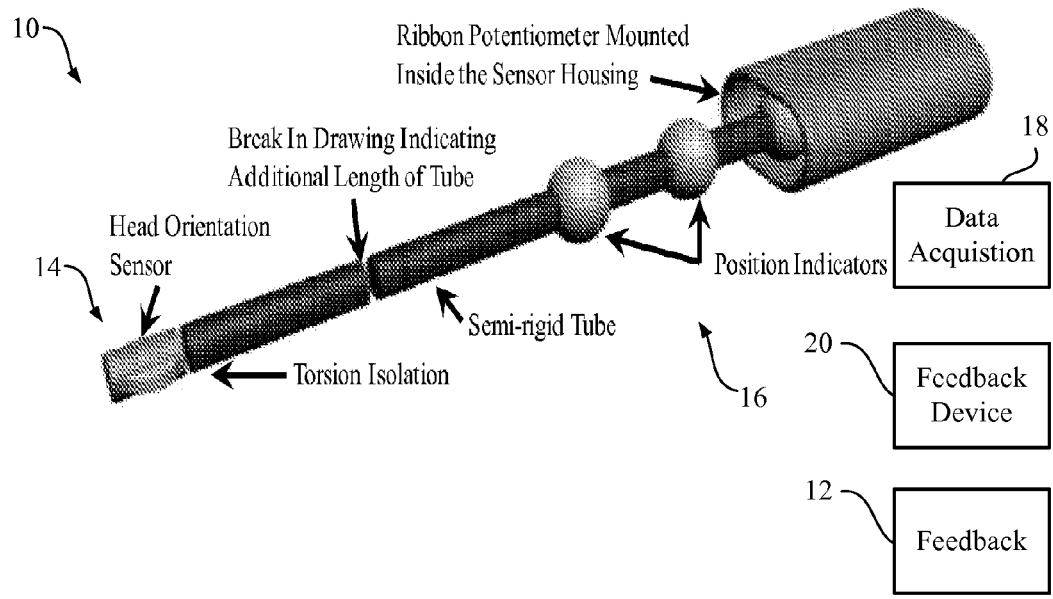
FIG. 1 is a drawing of one embodiment of the device using a ribbon potentiometer to measure fetal head position and rate of descent. A ribbon potentiometer mounted inside its sensor housing sends a voltage signal corresponding to the location of the current position indicator it is in contact with. The position indicators mounted around a semi-rigid tube affixed at the opposite end to the infants head moves through the position sensor at a rate equal to the rate of descent. The scalp attachment device is isolated from torsion forces using a break in the semi-rigid tube. The attachment portion of the device is kept aligned with the measurement portion of the tube with the lead wires running through the length of the device. An infant head orientation sensor is mounted as close to the scalp as possible.
Figure 2:
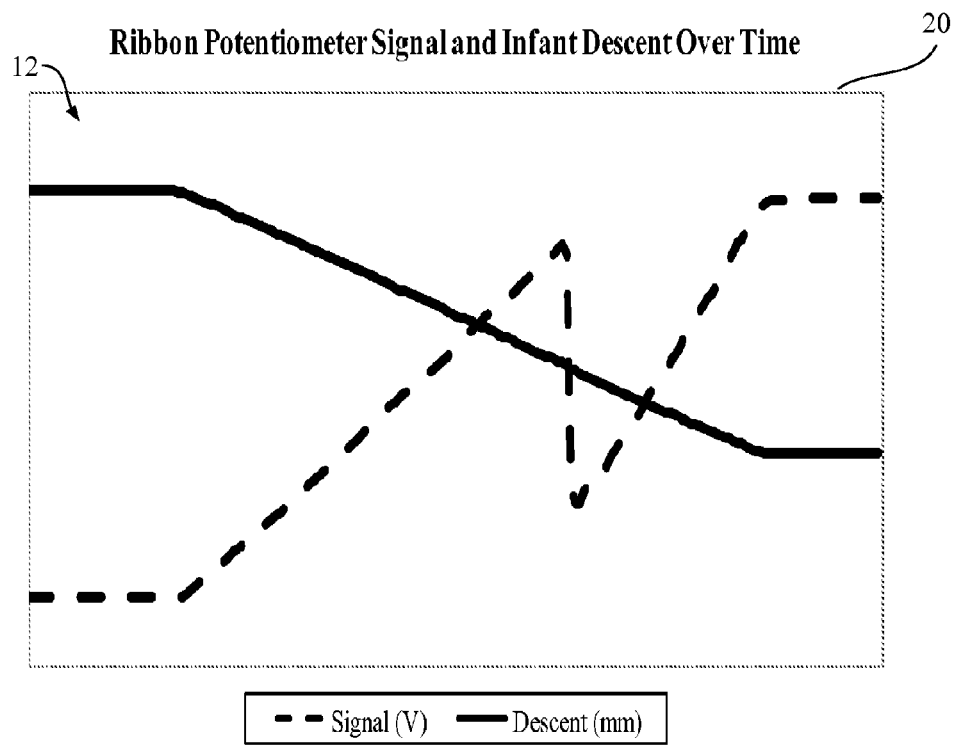
FIG. 2 is a graphical representation of the feedback signal from the device and the corresponding distance of infant descent. There are multiple peaks for the potentiometer for a constant descent. Due to size constraints of the measurement device, the ribbon potentiometer is used with multiple position indicators and the signal is logically translated to display actual descent.

Referring to FIGS. 1 and 2, in one aspect, a feedback system 10 provides feedback 12, such as real-time fetal position, movement velocity, and head orientation feedback, to professional medical staff and delivering mothers. Using this feedback 12, the mother can be apprised of how effective her pushing is moving the baby through the birth canal. Medical staff can use this feedback 12 to assess fetal head orientation and determine location of the baby in the birth canal. The feedback system 10 includes metrology devices, such as an orientation measurement device 14 configured to measure fetal head orientation, which may be mounted on a fetal scalp electrode, and a displacement measurement device 16 configured to measure fetal descent and velocity. Further, system 10 includes a data acquisition mechanism 18, including software to interpret the metrology signals, and a feedback device 20, including feedback hardware, to output the feedback 12 to doctors and the mother.

In accordance with one embodiment of the present invention, two sensors are mounted on a fetal scalp electrode. The first sensor, a 3-axis accelerometer, is mounted close to the electrode as shown in FIG. 1.

A semi-rigid tube contains and protects the two wires required for the scalp electrode as well as the five wires needed for the accelerometer. The semi-rigid tube is physically isolated from the scalp electrode as shown in FIG. 1. This isolation allows the tube to rotate without applying torsion force to the electrode affixed to the head of the baby. The tube is long enough to protrude 100 cm out of the mother's vagina.

At the end of the tube farthest from the scalp electrode, four molded beads are bonded around the outer diameter with a pitch of 25 mm as shown in FIG. 1. The diameter of the beads is 3 mm larger than the outer diameter of the tube. This tube is fed through a position sensor mounted with tape to the mother's thigh as shown in FIG. 1. The position sensor consists of an external housing that serves as a guide for the tube and a pressure-sensitive ribbon potentiometer mounted inside the housing. The inner diameter of the housing is designed so that the beads around the tube apply a slight normal force on the ribbon potentiometer. The length of the housing and the potentiometer is 20 cm.

The three axis feedback leads from the accelerometer as well as the position feedback lead from the ribbon potentiometer are connected to a data acquisition system. Power and ground leads for both sensors are also connected.

Once the apparatus is installed, the actual orientation of the head position will need to be defined relative to the accelerometer. This is accomplished through a graphical user interface.

During the delivery process, feedback is provided to the mother and the medical staff. The feedback is differentiated to suit the needs of the recipients.

For the benefit of the medical staff, fetal head orientation, decent and velocity are displayed in real time. This allows timely assessment and appropriate intervention that optimizes maternal and fetal outcome.

Feedback regarding fetal descent and velocity are also provided to the mother using visual, tactile and auditory means. The exact nature and combination of these feedback modalities can be selected by the mother.

This feedback compensates for the diminished natural sensation from anesthesia and is helpful to the mother by providing a real-time indication of the effectiveness of her expulsive efforts, thus shortening the delivery process.

After the delivery process is completed, all of the metrology hardware can be discarded.

The invention claimed is:

1. A method of feedback to a mother during labor, comprising:
   measuring fetal descent within a birth canal;
   processing, via a data acquisition system, data representing the measured fetal descent to generate substantially continuous fetal descent feedback during a contraction; and
   facilitating effective expulsive efforts by providing feedback directly to the mother during the same contraction, wherein the feedback represents the fetal descent feedback.

2. The method of claim 1, wherein the providing of the feedback to the mother further comprises a real-time indication of effectiveness of expulsive efforts in moving a baby through the birth canal.

3. The method of claim 1, further comprising:
   measuring fetal velocity corresponding to the fetal descent;
   processing data representing the measured fetal velocity to generate fetal velocity feedback; and
   wherein the feedback further represents the fetal velocity feedback.

4. The method of claim 1, wherein providing the feedback comprises providing visual feedback.

5. The method of claim 4, wherein providing the visual feedback further comprises providing a change in at least one of shape, color, intensity, persistence, size, or object movement.

6. The method of claim 1, wherein providing the feedback comprises providing auditory feedback.

7. The method of claim 6, wherein providing the auditory feedback further comprises providing a change at least one of volume, intensity, tone, beat, or content.

8. The method of claim 6, wherein providing the auditory feedback further comprises providing at least one of a tone, a voice, or music.

9. The method of claim 1, wherein providing feedback comprises providing tactile feedback.

10. The method of claim 9, wherein providing the tactile feedback further comprises at least one of a vibration or pressure.

11. The method of claim 1, further comprising:
    measuring fetal head orientation;
    processing data representing the measured fetal head orientation to generate fetal head orientation feedback; and
    wherein the feedback further represents the fetal head orientation feedback.

12. The method of claim 11, wherein providing the feedback further comprises generating a visual representation of the fetal head orientation feedback in 2 axes or 3 axes.

13. The method of claim 11, wherein measuring the fetal head orientation further comprises measuring via an accelerometer.

14. The method of claim 1, wherein measuring the fetal descent further comprises measuring via an optical system that measures a linear movement of a fetal head with respect to a fixed point outside of the birth canal.

15. The method of claim 1, wherein measuring the fetal descent further comprises measuring a linear movement of a fetal head with respect to a fixed point outside of the birth canal via at least one of:
    a potentiometer;
    a magnetic reader; or
    an ultrasonic position sensor.

16. The method of claim 1, wherein measuring the fetal descent further comprises measuring relative to a component disposed within the birth canal.

17. A labor feedback apparatus that provides feedback to a mother, comprising:
    a displacement monitor device to measure fetal descent within a birth canal;
    a data acquisition system to process data representing the measured fetal descent to generate substantially continuous fetal descent feedback during a contraction; and
    a feedback device to facilitate effective expulsive efforts by providing feedback directly to the mother during the same contraction, wherein the feedback represents the fetal descent feedback.

18. The feedback apparatus of claim 17, wherein the feedback to the mother further comprises a real-time indication of effectiveness of expulsive efforts in moving a baby through the birth canal.

19. The feedback apparatus of claim 17, further comprising:
    wherein the displacement monitor device further measures fetal velocity corresponding to the fetal descent;
    wherein the data acquisition system further processes data representing the measured fetal velocity to generate fetal velocity feedback; and
    wherein the feedback further represents the fetal velocity feedback.

20. The feedback apparatus of claim 17, wherein the feedback device provides the feedback comprising visual feedback.

21. The feedback apparatus of claim 20, wherein the feedback device provides the visual feedback comprising a change in at least one of shape, color, intensity, persistence, size, or object movement.

22. The feedback apparatus of claim 17, wherein the feedback device provides the feedback comprising auditory feedback.

23. The feedback apparatus of claim 22, wherein the feedback device provides the auditory feedback comprising a change in at least one of volume, intensity, tone, beat, or content.

24. The feedback apparatus of claim 22, wherein the feedback device provides the auditory feedback comprising at least one of a tone, a voice, or music.

25. The feedback apparatus of claim 17, wherein the feedback device provides the feedback comprising tactile feedback.

26. The feedback apparatus of claim 25, wherein the feedback device provides the tactile feedback comprising at least one of a vibration or pressure.

27. The feedback apparatus of claim 17, further comprising:
   an orientation measurement device configured to measure fetal head orientation;
   wherein the data acquisition system is further configured to process data representing the measured fetal head orientation to generate fetal head orientation feedback; and
   wherein the feedback further represents the fetal head orientation feedback.

28. The feedback apparatus of claim 27, wherein the feedback device is further configured to generate a visual representation of the fetal head orientation feedback in 2 axes or 3 axes.

29. The feedback apparatus of claim 27, wherein orientation measurement device comprises an accelerometer.

30. The feedback apparatus of claim 17, wherein the displacement monitor device further comprises an optical system that measures a linear movement of a portion of the optical system affixed to a fetal head with respect to a fixed point outside of the birth canal.

31. The feedback apparatus of claim 17, wherein the displacement monitor device measures a linear movement of a portion of displacement monitor device affixed to a fetal head with respect to a fixed point outside of the birth canal, and wherein the displacement monitor device further comprises at least one of:
   a potentiometer;
   a magnetic reader; or
   an ultrasonic position sensor.

32. The feedback apparatus of claim 17, wherein the displacement monitor device comprises a component disposed within the birth canal.

* * * * *